US010287543B2

(12) United States Patent
Poggel et al.

(10) Patent No.: US 10,287,543 B2
(45) Date of Patent: May 14, 2019

(54) PROCESS AND DEVICE FOR ISOLATING CELLS FROM BIOLOGICAL TISSUE

(71) Applicant: Miltenyi Biotec GmbH, Bergisch Gladbach (DE)

(72) Inventors: Carsten Poggel, Cologne (DE); Andreas Bosio, Cologne (DE); Wolfgang Stoters, Mulheim-Mintard (DE); Timo Adams, Odenthal (DE)

(73) Assignee: Miltenyi Biotec, GmbH, Bergisch Gladbach (DE)

( * ) Notice: Subject to any disclaimer, the term of this patent is extended or adjusted under 35 U.S.C. 154(b) by 205 days.

(21) Appl. No.: 15/333,337

(22) Filed: Oct. 25, 2016

(65) Prior Publication Data
US 2017/0145369 A1 May 25, 2017

(30) Foreign Application Priority Data
Nov. 19, 2015 (EP) .................................... 15195336

(51) Int. Cl.
*C12M 1/00* (2006.01)
*C12M 3/00* (2006.01)
(Continued)

(52) U.S. Cl.
CPC ............ *C12M 29/16* (2013.01); *C12M 21/08* (2013.01); *C12M 21/18* (2013.01); *C12M 23/28* (2013.01);
(Continued)

(58) Field of Classification Search
CPC ...... C12M 21/08; C12M 35/04; C12M 21/10; A01N 1/0242
See application file for complete search history.

(56) References Cited

U.S. PATENT DOCUMENTS 5,197,483 A * 3/1993 Rogalsky ............... A61B 10/02
  241/169.2
5,262,128 A * 11/1993 Leighton ............... B01L 3/0244
  422/522
(Continued)

FOREIGN PATENT DOCUMENTS

EP        2749306        7/2014
WO    WO2014/047287 A1    3/2014

OTHER PUBLICATIONS

Howard and Pesch, "The Enzymatic Preparation of Isolated Intact Parenchymal Cells From Rat Liver" J Cell Biol 35, (1967) pp. 675-684.
(Continued)

*Primary Examiner* — Nathan A Bowers
(74) *Attorney, Agent, or Firm* — Jaquelin K. Spong

(57) ABSTRACT

The invention is directed to a Perfusion device for biological tissues comprising
  a casing having two parts, a first part (1) and a second part (9),
  a holder (7) for a plurality of hollow penetration structures (8), wherein the hollow penetration structures (8) are provided with at least one orifice having fluid communication through the holder (7)
  a support (5) for the biological tissue (6)
    characterized in that the support (5) for the biological tissue (6) is positioned in the casing at a distance to the holder (7) that by joining the first part (1) and the second part (9) to form the casing, the hollow penetration structures (8) are in proximity to the holder (7).
Use of the perfusion device in a process for disaggregation of a biological tissue to yield target cells.

15 Claims, 12 Drawing Sheets

(51) Int. Cl.
  *G01N 1/28* (2006.01)
  *C12M 1/40* (2006.01)
  *C12M 1/34* (2006.01)
  *C12N 5/00* (2006.01)

(52) U.S. Cl.
  CPC ............ *C12M 23/46* (2013.01); *C12M 29/04* (2013.01); *C12M 29/10* (2013.01); *C12M 41/32* (2013.01); *C12M 45/00* (2013.01); *C12N 5/0081* (2013.01); *G01N 1/286* (2013.01)

(56) References Cited

U.S. PATENT DOCUMENTS

| | | | | |
|---|---|---|---|---|
| 6,286,455 | B1* | 9/2001 | Williams | A01K 45/007 119/6.8 |
| 6,689,103 | B1 | 2/2004 | Palasis | |
| 7,226,439 | B2* | 6/2007 | Prausnitz | A61B 5/14514 604/506 |
| 8,349,554 | B2 | 1/2013 | Bahrami et al. | |
| 8,366,677 | B2 | 2/2013 | Kaspar et al. | |
| 9,017,289 | B2* | 4/2015 | Backes | A61M 37/0015 604/173 |
| 2003/0060780 | A1* | 3/2003 | Shu | A61M 37/00 604/257 |
| 2004/0000901 | A1* | 1/2004 | Sui | G01N 33/48728 324/200 |
| 2004/0243157 | A1* | 12/2004 | Connor | A61B 17/320016 606/159 |
| 2005/0084954 | A1* | 4/2005 | Bader | C12M 23/38 435/295.1 |
| 2007/0021717 | A1* | 1/2007 | Gabel | A61M 5/14248 604/93.01 |
| 2007/0038181 | A1* | 2/2007 | Melamud | A61B 17/3478 604/158 |
| 2007/0065936 | A1* | 3/2007 | Hasegawa | C12M 23/48 435/288.7 |
| 2007/0239099 | A1* | 10/2007 | Goldfarb | A61N 1/327 604/20 |
| 2008/0255004 | A1 | 10/2008 | Neurauter et al. | |
| 2010/0152662 | A1 | 6/2010 | Boyden et al. | |
| 2011/0213335 | A1 | 9/2011 | Burton et al. | |
| 2011/0282239 | A1* | 11/2011 | Conlon | A61B 10/0275 600/566 |
| 2011/0295149 | A1 | 12/2011 | Mitragotri et al. | |
| 2012/0202715 | A1* | 8/2012 | Partida-Sanchez | B01L 3/50255 506/23 |
| 2015/0359967 | A1* | 12/2015 | Steel | A61M 5/345 604/192 |
| 2017/0258054 | A1* | 9/2017 | Smaal | A01K 43/00 |
| 2018/0265829 | A1* | 9/2018 | Kim | C12M 1/12 |

OTHER PUBLICATIONS

Berry and Friend, "Isolated Rat Liver Parenchymal Cells" (1969) J Cell Biol 43, 506-520.

Gomez-Lechon and Castell, "Isolation and culture of human hepatocytes" in Berry and Edwards, the Hepatocyte Review, (2000), pp. 11-15.

Seglen, "Preparation of Isolated Rat Liver Cells" (1976) Methods Cell Biol. 13, pp. 29-34.

Klaunig, "Mouse Liver Cell Culture" (1981) In Vitro 17, pp. 913-925.

\* cited by examiner

PROCESS AND DEVICE FOR ISOLATING CELLS FROM BIOLOGICAL TISSUE

CROSS REFERENCE TO RELATED APPLICATIONS

This application claims priority to European Patent Application EP15195336.1 filed on Nov. 19, 2015.

STATEMENT REGARDING FEDERALLY SPONSORED RESEARCH

Not applicable.

STATEMENT REGARDING MICROFICHE APPENDIX

Not applicable.

BACKGROUND

The present invention is directed to a process for isolating living target cells from biological tissue.

Cells which are strongly interconnected to form a biological tissue like epithelial cells are difficult to isolate into single, living cells from the tissue. While it is possible to mechanically destroy the infrastructure of the biological tissue and isolate single cells from the resulting debris, the thus obtained yield of living, unharmed cells is rather low.

It is known to isolate cells from organs in a more gentle perfusion process, but this requires cumbersome perfusion of the organ through an appropriate blood vessel with a sequence of buffer solutions. Such processes are known for the isolation of cardiomyocytes, or hepatocytes etc.

The procedure to isolate intact hepatocytes was first introduced by Howard and Pesch (1967) J Cell Biol 35, 675-684 and refined by Berry and Friend (1969) J Cell Biol 43, 506-520; Seglen (1976) Methods Cell Biol. 13, 29-34 and Klaunig (1981) In Vitro 17, 913-925. The outcome was a two-stage perfusion protocol which, after decades, still represents the current standard procedure leading to high amounts of viable hepatocytes. Usually, a loose ligature is placed around the appropriate blood vessel (rat: vena portae; mouse: vena cava) near the liver, a cannula is inserted into the blood vessel, and the ligature is fixed by tightening the thread ends. First, a calcium depleting buffer containing EDTA or EGTA is delivered into the organ through the blood vessel at a flow rate of about 10-15 ml/min for 10-15 min in order to weaken calcium-depending cell-cell junctions and remove blood cells. Second, a buffer comprising collagenase (at about 0.1 Wünsch Units per ml) is channeled (rat: 10-15 min; mouse: 5-10 min) through the organ at a flow rate of about 10-15 ml/min for destruction of connective tissue further liberating cells without damaging target cells. The liver can now be removed from the animal and placed in an appropriate media on a petri dish. Tearing apart the liver capsule leads to the release of liberated hepatocytes which are further purified by filtration through a 100 μm nylon mesh filter and an (optionally repeated) low-spin centrifugation step (5 min 50 g at 4° C.) to enrich hepatocytes.

A similar but ex-vivo process is used for hepatocyte isolation from livers of bigger vertebrates and/or for the isolation of adult cardiomyocytes. In these applications, the target organ is excised before cannulating a blood vessel.

For the generation of human hepatocytes see review of Gomez-Lechon and Castell, "Isolation and culture of human hepatocytes" in Berry and Edwards, The Hepatocyte Review, (2000), 11-15. The tissue is put on ice as fast as possible and inspected for large vessels. Cannulae are inserted into the largest vessels of the cut surface and fixed with tissue glue. In a first step, the liver tissue is perfused extensively with an calcium-depleting buffer containing EGTA (or EDTA) at about 10 ml/catheter. In the second step, it is perfused at the same flow rate with an about 0.2 U/ml collagenase-containing enzyme mix until the tissue shows irreversible deformation. Mostly, the enzyme buffer is recirculated to reduce costs. After digestion, the liver tissue is gently dispersed with a spatula. Analogues to the rodent procedure, the cell suspension is filtered and hepatocytes are enriched by a (optionally repeated) low-spin centrifugation.

Cardiomyocytes are generated by the so-called Langendorff perfusion system. The heart is rapidly excised from the body and, under a microscope, a cannula is carefully inserted into the aorta and fixed with a ligature. Then, the heart is perfused with a calcium-free buffer to arrest contraction, followed by a collagenase-based enzyme solution to digest the extracellular matrix of the heart. After digestion, the heart is mechanically dissociated with forceps and cardiomyocytes are dispersed into a single-cell suspension.

Lung alveolar epithelial cells are isolated in a similar procedure by inserting and fixing a cannula in the trachea and applying appropriate buffer and enzymes.

US20110295149 discloses a device to solubilize tissue by an abrasive extraction of tissue fragments. The device is fixed on the tissue by vacuum and the cells are cut from the tissue with an abrasive component and further liquefied by appropriate enzymes.

In summary, the known isolation processes for cells from biological tissue are elaborate, time-consuming and are always executed by skilled personal.

In another technical field, it is known to inject pharmacological active compounds into tissue like skin through a plurality of cannulas. The cannulas can be assembled in arrays having a common input lumen, as for example disclosed in U.S. Pat. Nos. 6,689,103, 8,349,554B2, 8,366,677B2, 8,708,965B2, US2011/0213335A1, WO2014/047287A1 or EP2749306. These publications are silent on the dissociation of the tissue to generate single-cells.

SUMMARY

It was therefore an object of the invention to provide a device and a method for isolating living cells from biological tissue without the tedious and inconvenient need of cannulating a distinct lumen or cavity like a blood vessel.

It was surprisingly found that agents that release target cells from the biological tissue can be delivered by a device comprising a plurality of injection sites into a biological tissue, thereby releasing target cells as a single-cell suspension with good yield and viability of the target cells.

Object of the invention is therefore an perfusion device for biological tissues comprising a casing having two parts, a first part (1) and a second part (9); a holder (7) for a plurality of hollow penetration structures (8), wherein the hollow penetration structures (8) are provided with at least one orifice having fluid communication through the holder (7); a support (5) for the biological tissue (6); wherein the support (5) for the biological tissue (6) is positioned in the casing at a distance to the holder (7) that by joining the first part (1) and the second part (9) to form the casing, the hollow penetration structures (8) are in proximity to the holder (7).

The hollow penetration structures (8) may penetrate at least in part into the biological tissue (6) by manually pressing the holder with the hollow penetration structures (8) pointed against the biological tissue (6) which is located on the support (5). The penetration process may be triggered manually, but preferred by closing the casing. The first and second part of the casing are adapted or configured such that by joining the first part (1) and the second part (9) to form the casing, the hollow penetration structures (8) may penetrate at least in part into the biological tissue (6).

Another object of the invention is a process for disaggregation of a biological tissue with a device as disclosed wherein the biological tissue is penetrated at least in part by at least one of the hollow penetration structures (8) by joining the first part (1) and the second part (9) to form the casing and at least one agent to disaggregate the biological tissue into target cells is administered through the hollow penetration structures (8) into the biological tissue (6).

The term "disaggregation of a biological tissue into target cells" refers to any process where cell structures, cell aggregates or cell matrices are at least in part destroyed without killing, destroying or lysing the target cells. At best, the target cells are obtained as single, isolated and living cells. For example, if liver is used as biological tissue, an appropriate enzyme is administered into the liver with the device of the invention. The liver tissue is disaggregated to yield single liver cells which do not leave the liver. To harvest the target cells, the epithelial cell sheet of the liver (the capsule of the liver) is mechanically opened and the liver cells can be washed from the remaining tissue.

BRIEF DESCRIPTION OF THE DRAWINGS

Various exemplary details are described with reference to the following figures, wherein.

It should be understood that the drawings are not necessarily to scale, and that like numbers may refer to like features.

DETAILED DESCRIPTION

Figure 1:
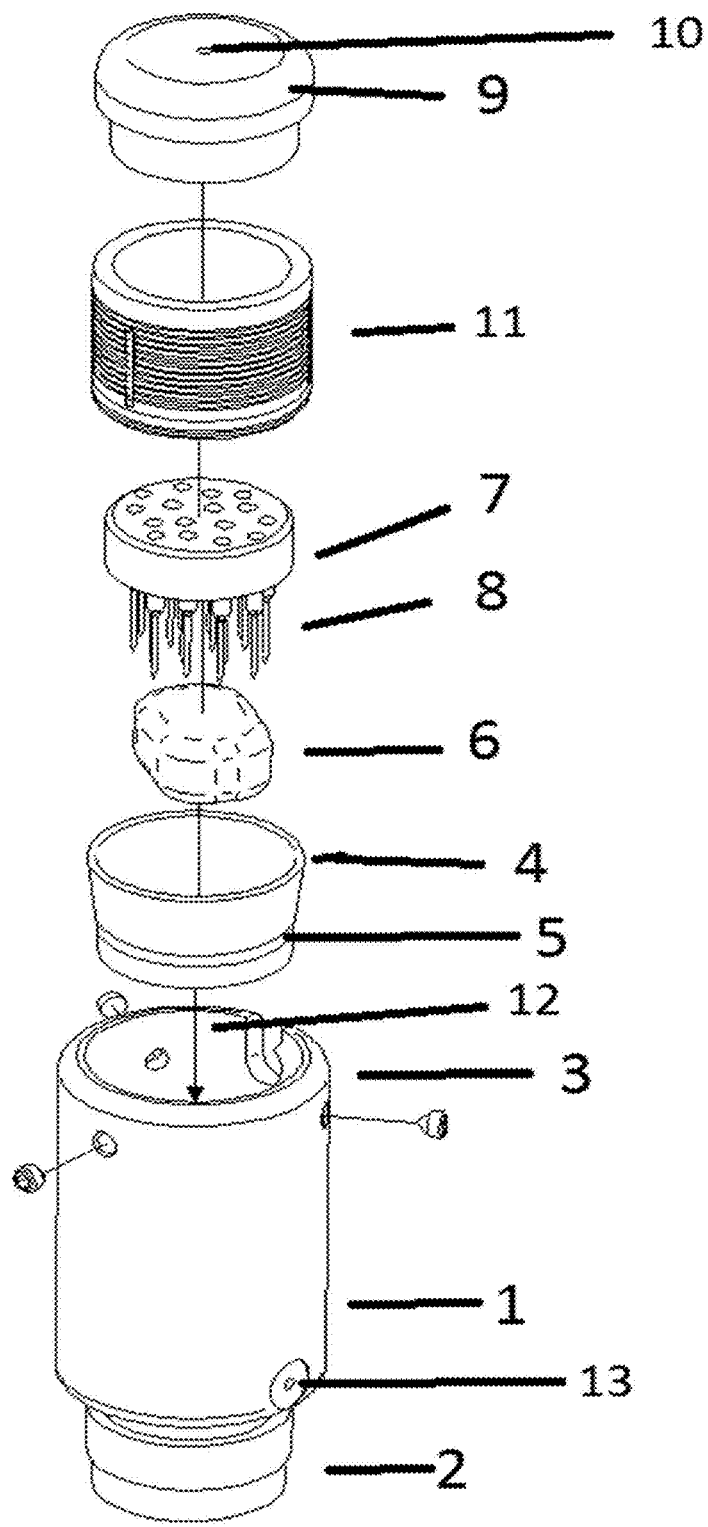
FIGS. 1, 2, and 3 show variants of a device of the invention, with casing having a first (1) and second part (9) each having a closing mechanism (11, 12); filter cage (4) and support (5) having a size or outer diameter fitting into the casing; holder (7) for a plurality of hollow penetration structures (8), also having a size or outer diameter fitting into the casing; hollow penetration structures (8) with fluidic connection through the holder (7); input/output port (11, 13)
Figure 2:
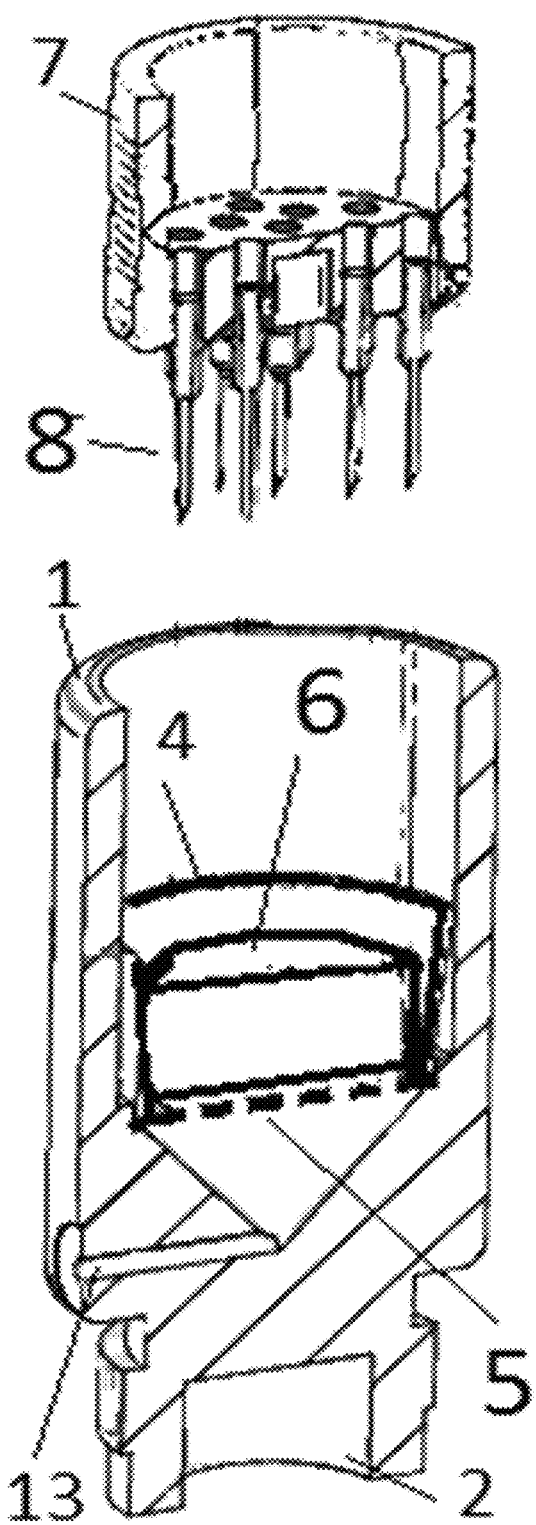
Figure 3:
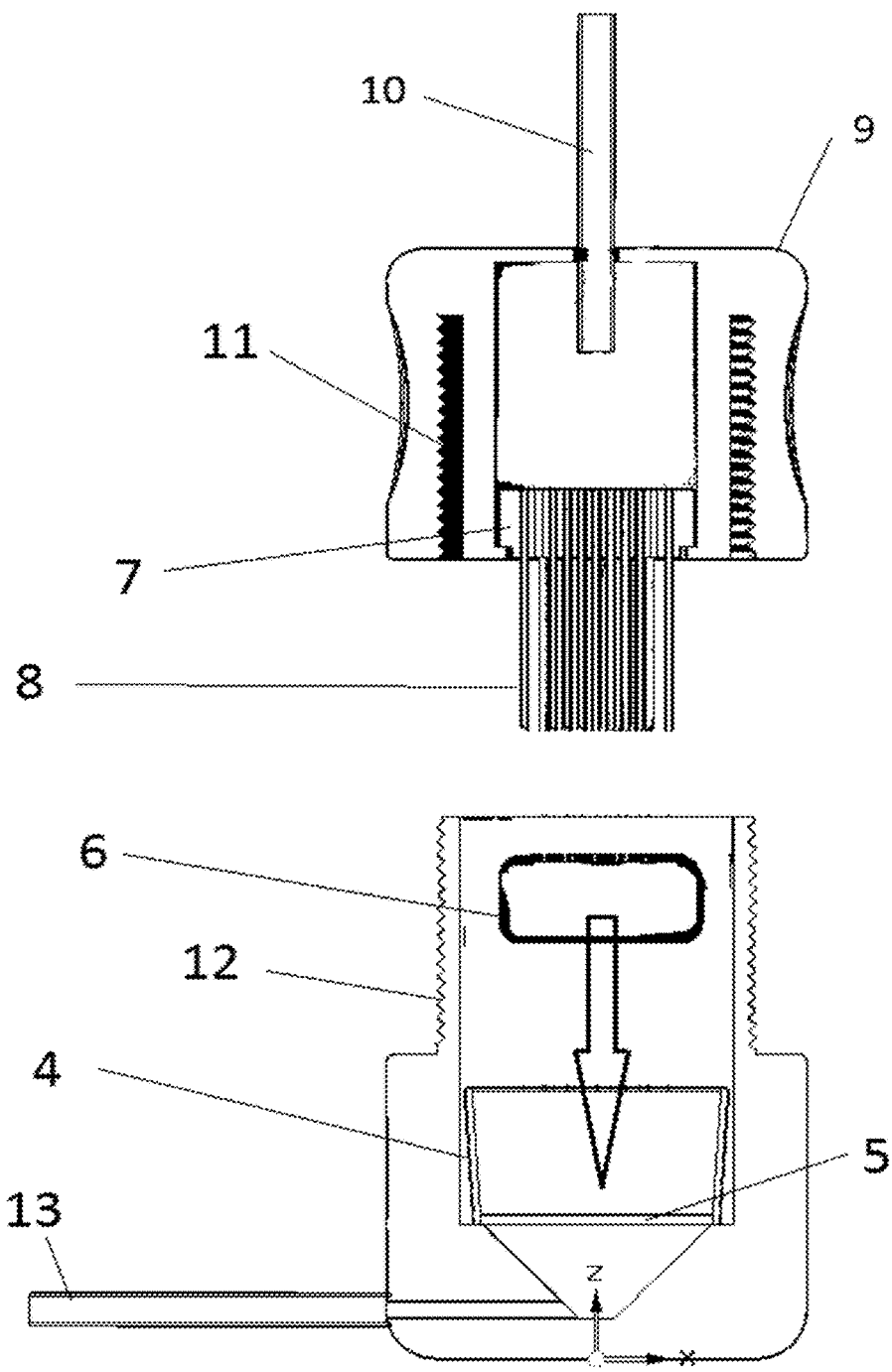
Figure 4:
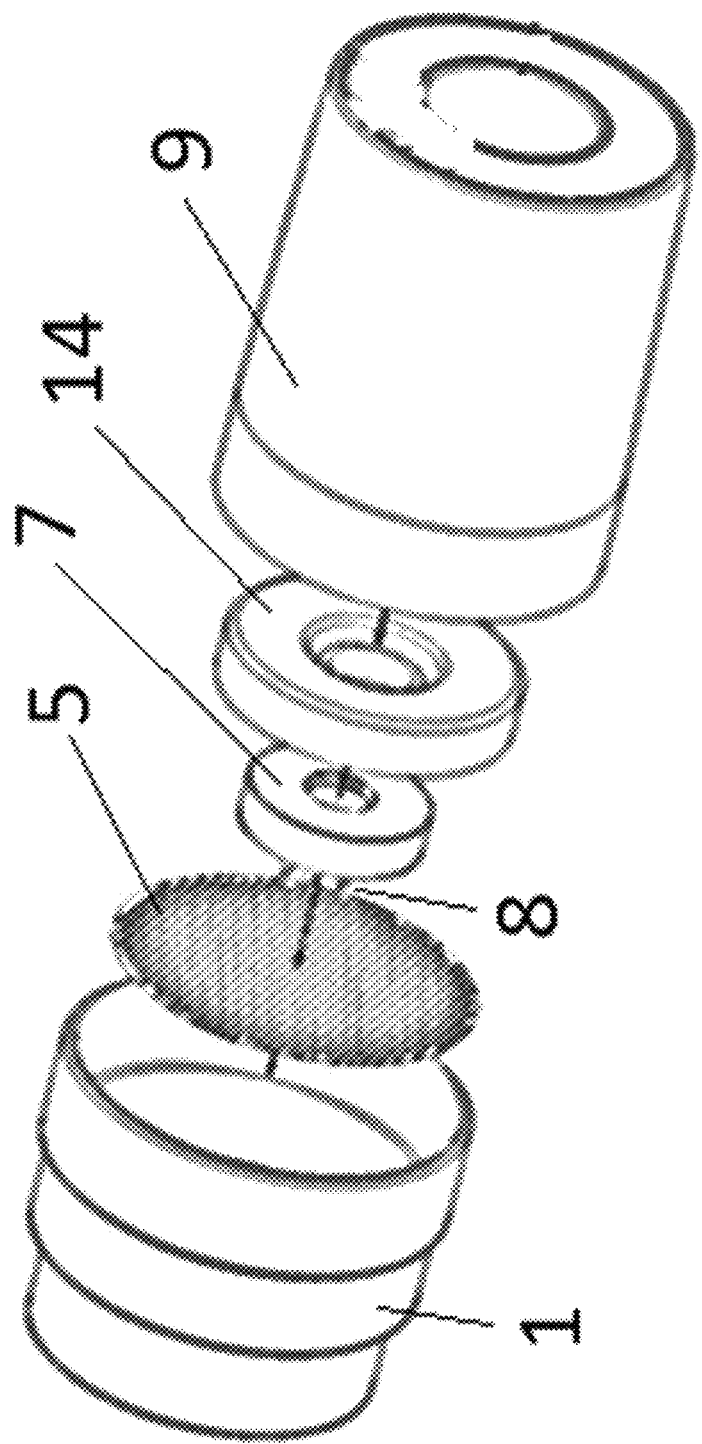
FIGS. 4 and 5 show further storage cavity (14) for fluids and an integrated pump (15)
Figure 5:
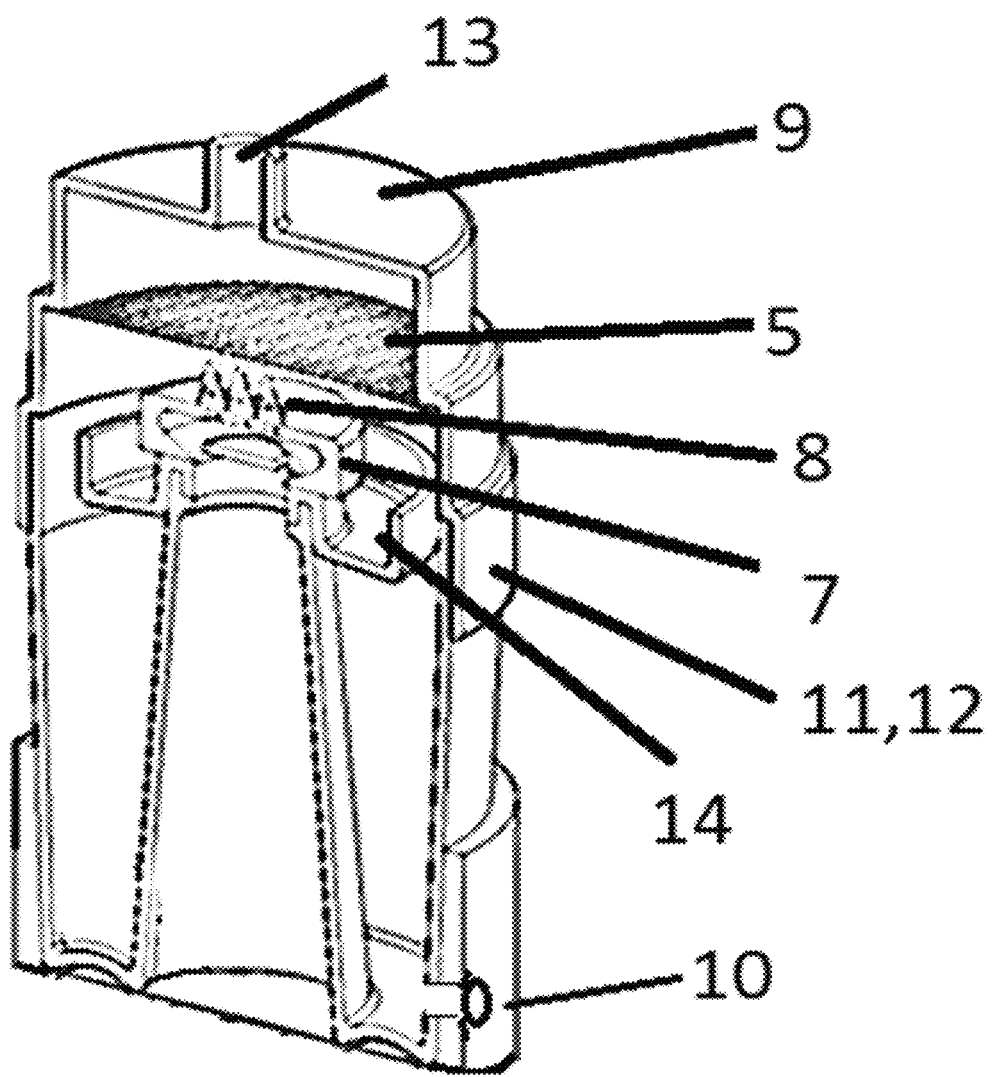

The cells achieved by the process and device of the present invention can be cultured, analyzed and/or transplanted into patients with methods known to a person skilled in the art.

Device of the Invention

The device of the invention is shown by way of example in several embodiments in FIG. 1 to FIG. 5.

In a preferred embodiment, the first part (1) and the second part (9) of the casing are each provided with a corresponding closing mechanism (11, 12) for joining the two parts.

In another embodiment, the first part (1) and/or the second part (9) of the casing are provided with at least one orifice for in- and/or output of fluids (10, 13). In this embodiment, the hollow penetration structures (8) are provided with at least one orifice having fluid communication through the holder (7) to at least one of these orifices (10, 13).

The casing of the device can be opened and closed in preferable a water-tight manner by the corresponding closing mechanism of the first and second part of the casing. The corresponding closing mechanisms (11,12) of the first part (1) and the second part (9) of the casing may be threads, bayonet mounts, cone closings, twist closings, magnets or bold heads, each capable of interlocking or joining the first and second part to form the casing. Furthermore, one of the first and second part of the casing can be constructed as flip cover or a hinged cap with an appropriate closing mechanism on the respected other part of the casing.

The first and second part of the casing, the closing mechanism (11, 12) and the holder (7) may be combined to one or two separate pieces, but can also be provided separately. If the first and second part of the casing and one or both closing mechanisms (11, 12) are separate devices, they need to be provided with means like apertures to enable mechanically combination when closing the device.

The biological tissue is placed on the support (5) which permeable for fluids and is then pressed between the support and the penetration needles (i.e. the holder), resulting in penetration of the biological tissue at least in part by the hollow penetration structures (8).

Support (5) serves as counterpart for the holder (7) when the penetration structures are pressed against the tissue. To this end, the tissue may be placed on the support and pressed against the penetration structures or the tissue may be placed on the penetration structures and pressed against the support.

The support (5) may be an integral part of the casing (i.e. the first or second part) or may be inserted and removed from the casing. In the latter case the support needs to have a smaller diameter that the casing. The support (5) has the function of providing a mechanical counterpart to the holder (7) when the needles penetrate into the tissue. Insofar, the design of support (5) is not essential and may be provided in form of a filter, mesh, rack, grid or even a plate with orifices (in order to prevent the tissue being soaked in fluids).

The holder (7) can be inserted and removed from the casing i.e. should have a size or outer diameter fitting into the main casing. Preferable, the holder (7) has a size or outer diameter to fit in a water-tight manner into the casing and/or is provided with an appropriate seal to prevent fluids (release agents) from circumventing the holder/the hollow penetration structures (8).

The term "hollow penetration structures" refer to any elongated object having a needle-, cone- or pyramid-like shape, which is provided with a sharpened end. In the following, the term "hollow penetration structures" and "needle" is used as synonym.

The hollow penetration structures and the holder may be produced separately or as one piece.

Preferable, the hollow needles (8) are provided with means to stop the flow of reagents through a needle when the opening of a needle is placed not within the biological tissue, i.e. in case a needle did not penetrate into the tissue or penetrated through the tissue.

The hollow penetration structures (8) may have an outer diameter at the basis of 0.05 to 5 mm, preferably 0.2 to 1 mm, most preferably 0.3 to 0.7 mm and independently, an inner diameter at the basis of 0.02 to 4 mm, preferably 0.1 to 1 mm, most preferably 0.1 to 0.6 mm and independently a length of 1 to 100 mm, preferably 2 to 20 mm, most preferably 4 to 5 mm.

The number of hollow penetration structures (8) depends on the size of the biological tissue and may vary between 2 and 500, preferably between 5 and 100, and most preferably between 20 and 70. The hollow penetration structures (8) may be arranged in any geometry or array on the holder and may have the same or different length. The holder may be not mechanically fixed in main casing. This enables the use of different holders with different number of hollow penetration structures (8) and/or different length of hollow penetration structures (8) and/or different geometry or array of hollow needles on the holder, depending on the size and thickness of the biological tissue.

Depending on the size, thickness and the outer form of the biological tissue, the number, length, outer/inner diameter and area of hollow penetration structures (8) can be selected to achieve maximum effect of penetration.

The device of the invention, i.e. the casing comprising the first and second part, the holder (7) and the hollow penetration structures (8) may be produced from the same or different material like stainless steel, polyacrylamide, polystyrene, polyolefins like polyethylene and polypropylene, polycarbonate, polyoxymethylene, polymethylmethacrylate, poly lactic acid or polyamides.

The device of the invention may be manufactured by any method known to a person skilled in the art. Preferred methods are injection molding and 3D printing, for example by extrusion deposition, fused deposition modeling, stereolithography or photopolymer digital light processing.

The perfusion device according to the invention has the advantage that only the parts having mechanical contact to the biological tissue, i.e. the holder for the plurality of hollow needles and the support, are single-use disposables, whereas the main casing and the cap can, after appropriate cleaning, be used multiple times. In a variant, of the invention, the device is provided as disposable.

The perfusion device, according to the invention, may be used manually, i.e. with syringes and appropriate vessels, but can also be used in an automated environment comprising one or more pumps and tubing sets.

Figure 10:
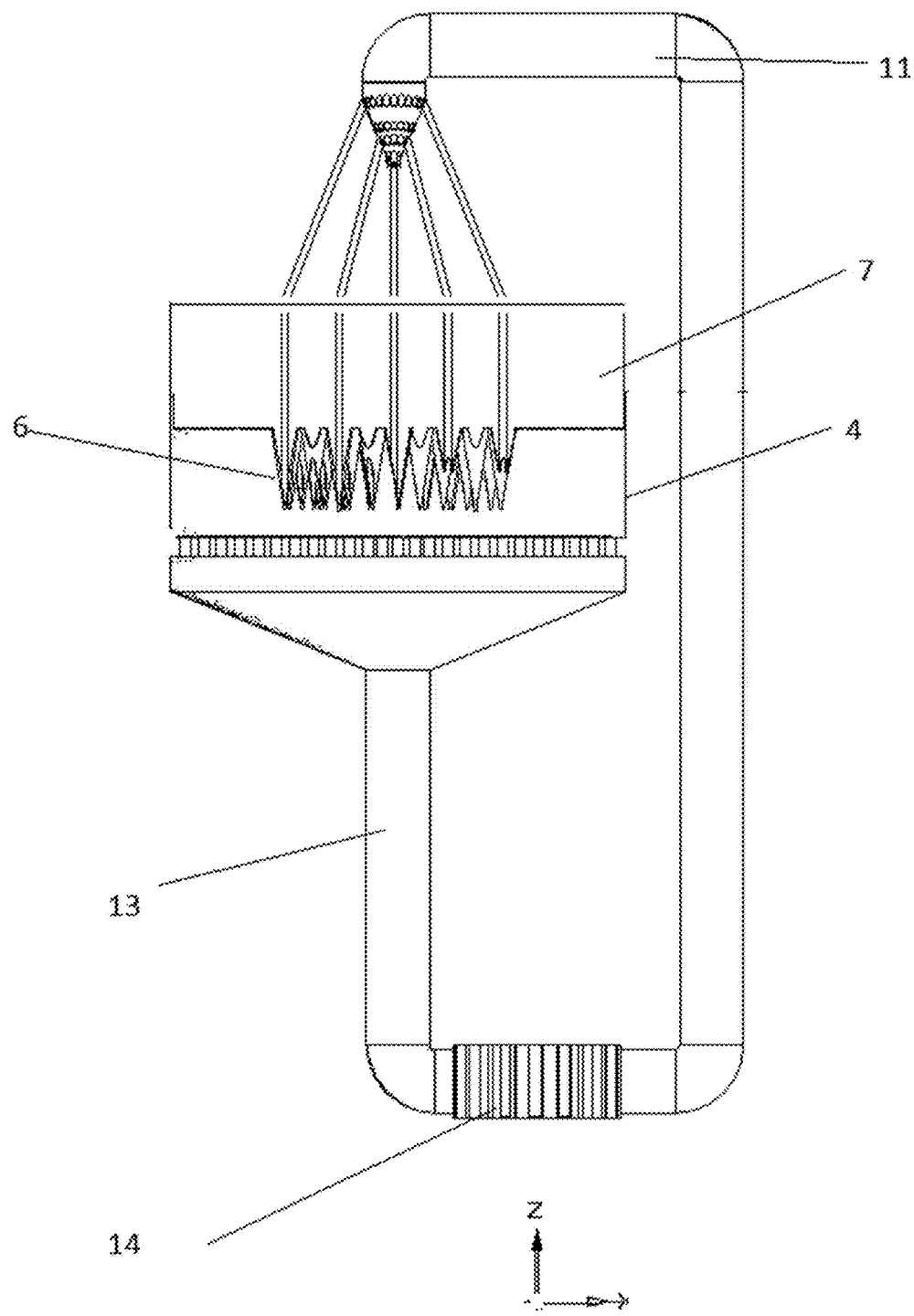
FIG. 10 shows further storage cavity (14) for fluids and an integrated pump (15)

In another embodiment, the device is provided with at least one pump, like a gear pump as shown in FIG. 10. The pump may be directly connected to the input/output orifices of the casing or may be provided with filter system or detection devices to monitor the release process of the cells. The pump may be integrated in the casing either in the first or the second part of the casing, or can provided externally and connected to the device with an appropriate tubing set. The position of the pump in view of the biological is not of importance. The pump may be driven by an internal or external motor. If the pump is integrated into the first or the second part of the casing, the pump and the casing are preferable manufactured by a 3D printing manufacturing process as disclosed for the holder (7).

Process of the Invention

The process of the invention is characterized in that the biological tissue is penetrated at least in part by a plurality of hollow penetration structures (8). The term "penetration" as used herein means that the needles are placed into the biological tissue in order to administer the release agent into the biological tissue. It is not desired to pierce or puncture the needles through the biological tissue since the release agent would then not or not sufficiently enter the biological tissue to release the target cells. It should be taken care in the process of the invention that the majority of the needles are placed inside the biological tissue and do not pierce or puncture through the biological tissue. At best, all needles are placed into the biological tissue at 30-70%, preferable approximately 50% of its thickness.

In the process of the invention, the biological tissue is pressed between a support (5) permeable for fluids and the needles, resulting in penetration of the needles at least in part into the biological tissue. The support (5) can be for example the filter area of a filter cage (4), for example a "Smart Strainer" filter cage commercialized by Miltenyi Biotec GmbH.

In one embodiment of the process according to the invention, the biological tissue is penetrated by the plurality of hollow needles by placing the tissue on a support, e.g. a mesh of a filter cage of a device as already disclosed, closing the main casing with the cap and administering at least one agent to disaggregate the biological tissue through at least one orifice of the cap and collecting the flow-through from at least one orifice at another, preferably the lower end of the main casing.

In a variant of the invention, at least one agent is administered into the biological tissue in an amount that an excess volume of release agent leaks from the biological tissue, and said excess volume of agent is administered again into the biological tissue. The term "excess volume" means that compared to the volume of the biological tissue, a much greater volume of agent is administered, and the volume of agent not taken up by the biological tissue leaks out. This embodiment may involve the administering of the agents in a first fresh stream which is recycled either as constant leak stream or batch-wise into the biological tissue.

The leak stream may already contain target cells. In this variant, the leak stream may be collected as cell suspension after one or more cycles.

The process of the invention may be applied to a great variety of biological tissues. However, depending on the preparation and the macroscopic nature of the biological tissue, the target cells are disintegrated from the cellular infrastructure of the biological tissue by administering the agent, but cannot be released/extracted from the biological tissue and/or leave the biological tissue. This might occur if the outer structure of the biological tissue is still intact or if the biological tissue is provided with a capsule. e.g. an epithelial cell sheet. Extracting target cells from such biological tissue requires mechanically opening of the capsule.

In another embodiment of the invention, after administering of at least one release agent into the biological tissue, the biological tissue is mechanically opened and the target cells are extracted from the biological tissue. In variants of this embodiment, the biological tissue is mechanically opened by cutting, piercing, or rupturing the biological tissue manually by appropriate tools. In preferred variants, the device of the invention is provided with means for mechanically opening the biological tissue, for example with a cutting device built in the main casing, the filter cage or the support for hollow needles. In another variant, the hollow penetration structures are used as cutting device, for example by rotating the holder against the tissue.

The process may comprise an additional step to remove unwanted "non-target cells", e.g. blood cells, before administering at least one agent to disaggregate the biological tissue. In this step non-target cells are extracted from the biological tissue by administering at least one washing fluid into the biological tissue. In this variant of the process according to the invention, the biological tissue (6) is first washed with buffer to release non-target cells from the biological tissue (6) and the fluid containing the non-target cells are stored in the storage cavity (14).

In yet another variant, the agent to disaggregate the biological tissue (6) and/or the buffer is repeatedly administered into the biological tissue (6), for example by a pump. In this variant, the fluids are recycled several times over/into the biological tissue (6), thereby improving yield.

Target Cells

The process of the invention can be applied to generate all type of target cells which are tissue-resident cells, especially cells from vertebrate or invertebrate tissue, preferably epithelial cells, endothelial cells, fibroblasts, myofibroblasts, hepatocytes, hepatic stellate cells, cardiomyocytes, podocytes, keratinocytes, melanocytes, neuronal cells including neurons, astrocytes, microglia and oligodendrocytes, leukocytes including dendritic cells, neutrophils, macrophages and lymphocytes, including T cells, B cells, NK cells, NKT cells and innate lymphoid type 1-3 cells, tissue stem cells including MSCs and progenitor cells of cells mentioned above.

Biological Tissue

The process of the invention can be applied to all types of biological tissue, like organs of vertebrates or invertebrates, preferably to spleen, heart, liver, brain and other neural tissues, kidney, lung, pancreas, breast, umbilical cord, skin, placenta, ovary, oviduct, uterus, prostate, tonsil, thymus, stomach, testis, trachea, cartilage, tendon, bone, skeletal muscle, smooth muscle, gut, colon, intestine, bladder, urethra, eye, gall bladder, organoids from cell cultures and tumors.

Disaggregating Agents

The term "disaggregating agent" as used herein means a fluid like a buffer comprising a substance used to destroy the anchorage of target cells within the tissue without influencing the target cells itself. This anchorage derives from interactions of the cells with the extracellular matrix or with adjacent cells. These interactions, e.g. tight junctions, gap junctions, desmosomes, and hemidesmosomes, are built mainly by proteins, e.g. cadherins, connexins, claudins and integrins, mostly in a calcium-dependent manner Therefore, the release agent which destroys the tissue integrity may contain a calcium-free and/or a calcium-depleting agent and/or enzymes that degrade the extracellular matrix or extracellular protein-protein interactions. The administration of the components of the release agent may be sequentially or simultaneously.

For example, the agent to disaggregate the biological tissue (6) is selected from the group consisting of trypsin, chymotrypsin, papain, collagenase, elastase, dispase, thermolysin, hyaluronidase, clostripain and neutral protease from *clostridium histolyticum*, pronase, DNase I, pepsin, proteinase K, lysozyme, chelating agents for bivalent ions (like EDTA or citrate) and mixtures thereof.

Preferred is a sequestered application of a calcium-free or calcium-depleting buffer followed by an enzyme-containing buffer which degrades the extracellular matrix or extracellular protein-protein interactions. The calcium-depleting reagent may be a buffer containing EDTA, EGTA or citrate.

In another embodiments of the process according to the invention, a calcium-free buffer or a calcium-depleting buffer is used in a first step and a buffer containing calcium ions, preferably at least 50 μM calcium ions, as well as a calcium-depending enzyme is used in a second step.

Most preferably, a calcium-free buffer or a calcium-depleting buffer is used in a first step and a buffer concentrate containing calcium ions as well as a calcium-depending enzyme is spiked into the first buffer as a concentrate in a second step.

As buffer, any aqueous fluid with pH values, osmolality and ion concentrations in the physiological range can be used. Preferred buffers are PBS, D-PBS, HBSS (Hanks' balanced salt solution), EBSS, DMEM (Dulbecco's Modified Eagle Medium), DMEM/F12, IMDM, RPMI, RPMI-1640, either in a complete form or in variants thereof, with or without phenol red, with or without HEPES, with or without glucose, optionally including a protein component like FCS (fetal calf serum), FBS (fetal bovine serum), HSA (human serum albumin), or BSA (bovine serum albumin). The pH of the buffer is between 6.0 and 8.0, preferably between 7.0 and 7.5.

The first buffer administered to the tissue might contain an anticoagulant like EDTA, EGTA, citrate or heparin to avoid blood coagulation within the tissue.

Enzymes

In the process of the invention, a wide variety of enzymes, for example disclosed in Barry, Edwards and Barritt (1991) in Laboratory Techniques in Biochemistry and Molecular Biology Vol. 21 can be used. The following enzymes may be used as component in the release agents:

Collagenase (EC 3.3.24.3) from *Clostridium histolyticum*, also called clostridiopeptidase A, is an enzyme mixture capable of causing hydrolytic cleavage of collagen molecules in their native conformation and at their helical region. These enzymes are very specific to collagen and have a specificity for the Pro-X-Gly-Pro (X=neutral amino acid) motive. They require $Ca^{2+}$ for activity and usually contain $Zn^{2+}$. Collagenase can also be isolated from many other bacterial sources (e.g. *Achromobacter iophagus, Mycobacterium tuberculosis, Pseudomonas aeruginosa* and other microorganisms). However, *Clostridium histolyticum* provides the main commercial source of collagenase. Crude preparations also contain contaminating protease activities like clostripain, neutral protease and further tryptic, caseinase and lipase activities. These can hydrolyse the portions of collagen which are not tightly wound in the helical form. Differences in the relative quantities of these contaminating activities are responsible for observed lot-to-lot variation.

Hyaluronidase (EC 3.2.1.35), an endoglycosidase with a specificity for endo-N-acetylhexosaminic bonds, usually derives from bovine and sheep testis. It hydrolyses 1,4 linkages between 2-acetacido-2-deoxy-β-D-glucose and D-glucuronate residues in hyaluronic acid, a glycosaminoglycan found in the ground substance of virtually all connective tissue.

Trypsin (EC 3.4.21.4), a pancreatic serine protease, is capable of hydrolyzing peptides, preferentially at bonds involving the carboxyl group of the basic amino acids, L-arginine or L-lysine, and also shows some esterase and amidase activity. Purified trypsin is ineffective against native collagen and, therefore, not suitable for use by itself in the dissociation of adult liver tissue.

Clostripain (EC 3.4.22.8), like collagenase is derived from *Clostridium histolyticum* and highly specific for the carboxyl peptide bond of arginine. It is activated by calcium and found in commercial crude collagenase preparations.

Lysozyme (EC 3.2.1.17), an endoglycosidase, catalyses the hydrolysis of 1,4-β-linkages between N-acetylmuramic acid and N-acetylglucosamine residues in glycosaminoglycans.

Pronase (EC 3.3.24.4), a non-specific protease isolated from *Streptomyces griseus*, hydrolyses nearly all naturally occurring peptide bonds.

Dispase (EC 3.4.24.28), a protease produced by *Bacillus polymyxa*, is capable of cleaving fibronectin, collagen IV, and to a lesser extent collagen I and hydrolyzing bonds involving leucine or phenylalanine.

Pancreatic Elastase (EC 3.4.21.36), or elastase 1, a serin protease, degrades elastin, an elastic fibre which, together with collagen, determines the mechanical properties of connective tissue.

Thermolysin (EC 3.4.24.27), a thermostable neutral metalloproteinase produced by *Bacillus thermoproteolyticus*, which requires $Zn^{2+}$ for enzyme activity and four $Ca^{2+}$ for structural stability, has a molecular weight of 34.6 kDa and specifically catalyzes the hydrolysis of peptide bonds containing hydrophobic amino acids.

Papain (EC 3.4.22.2), a cysteine protease, is an enzyme derived from *papaya*.

Chymotrypsin (EC 3.4.21.1), a digestive enzyme component of pancreatic juice, digests proteins and polypeptides in the duodenum and preferentially cleaves peptide amide bonds at aromatic amino acids (tyrosine, phenylalanine and tryptophan). After being synthesized as an inactive precursor (chymotrypsinogen), it is activated by trypsin cleavage.

Proteinase K (EC 3.4.21.64), a 28.9 kDa broad-spectrum serine protease produced by *Engyodontium album* (formerly *Tritirachium album*), is capable of digesting hair keratin. It is commonly used in molecular biology to digest proteins thus removing contaminations from nucleic acids preparations.

Pepsin (EC 3.4.23.1), whose zymogen (pepsinogen) is released by the chief cells in the stomach, degrades food proteins into peptides. It is most efficient in cleaving peptide bonds between hydrophobic and preferably aromatic amino acids such as phenylalanine, tryptophan, and tyrosine.

DNase I (EC 3.4.21.1) is a nuclease that cleaves DNA preferentially at phosphodiester linkages adjacent to a pyrimidine nucleotide, yielding 5'-phosphate-terminated polynucleotides with a free hydroxyl group on position 3', on average producing tetranucleotides. It acts on single-stranded DNA, double-stranded DNA, and chromatin. Regarding tissue dissociation, DNase I is useful for reducing cell aggregation caused by free DNA.

In one embodiment of the process according to the invention, a calcium-free buffer is used in a first perfusion cycle and a buffer containing significant amounts of calcium, preferably at least 50 µM, as well as a collagenase from *Clostridium histolyticum*, preferably between 0.05 and 1 Wünsch Units, is used in the second. In another embodiment of the process according to the invention, a calcium-depleting buffer is used in a first cycle and a buffer containing significant amounts of calcium, preferably at least 50 µM, as well as a collagenase from *Clostridium histolyticum*, preferably between 0.05 and 1 Wünsch Units, is used in the second cycle.

Washing Fluid

The washing fluid used in the process of the invention may comprise an aqueous buffer with pH, osmolality and ion concentrations which are in the physiological range. Preferred buffers are PBS, D-PBS, HBSS (Hanks' balanced salt solution), EBSS, DMEM (Dulbecco's Modified Eagle Medium), DMEM/F12, IMDM, RPMI, RPMI-1640, either in a complete form or in variants thereof, with or without phenol red, with or without glucose, optionally including a protein component like FCS (fetal calf serum), FBS (fetal bovine serum), HSA (human serum albumin), or BSA (bovine serum albumin). The pH of the buffer is between 6.0 and 8.0, preferably between 7.2 and 7.4.

Use of the Method

The method and device of the invention can be used to isolate the above mentioned target cells from the appropriate biological tissues. The thus isolated target cells may be used for various applications in research, diagnostics and cell therapy. For example, hepatocytes, cardiomyocytes or primary cells isolated with the device and the method of the invention can be used in assays to investigate either themselves or their reactions with other cell types or analytes. Hepatocytes and cardiomyocytes are useful sources for toxicological screenings of chemicals, especially potential drug compounds. The device and method of the invention may further be used to isolate living cells for transplantation into injured organs or to create artificial organs or organoid-like structures.

Although the following examples are restricted to certain target cells and tissues, especially hepatocytes from liver, the scope of the invention shall not be limited to the examples as the device and the process can be used for dissociating any biological tissue of invertebrate or vertebrate origin.

EXAMPLES

Comparison Example 1

Commonly Used Perfusion of Mouse Liver

Figure 6A:
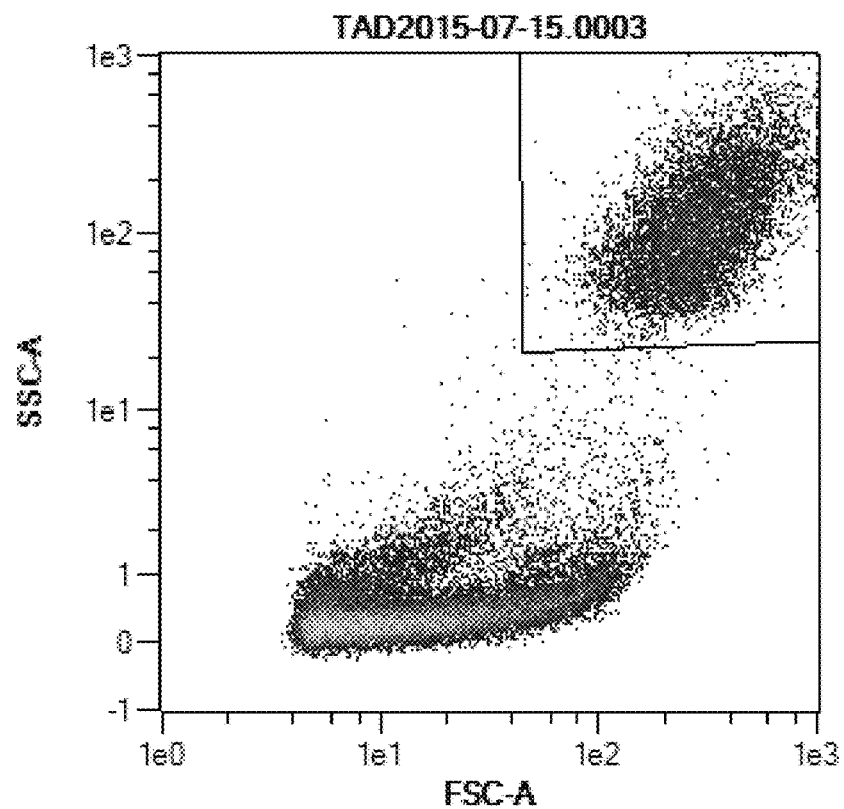
FIGS. 6a and 6b shows the flow cytometry analysis of mouse liver cells isolated by the state-of-the-art perfusion technique, with further hepatocyte enrichment by Percoll centrifugation.
Figure 6B:
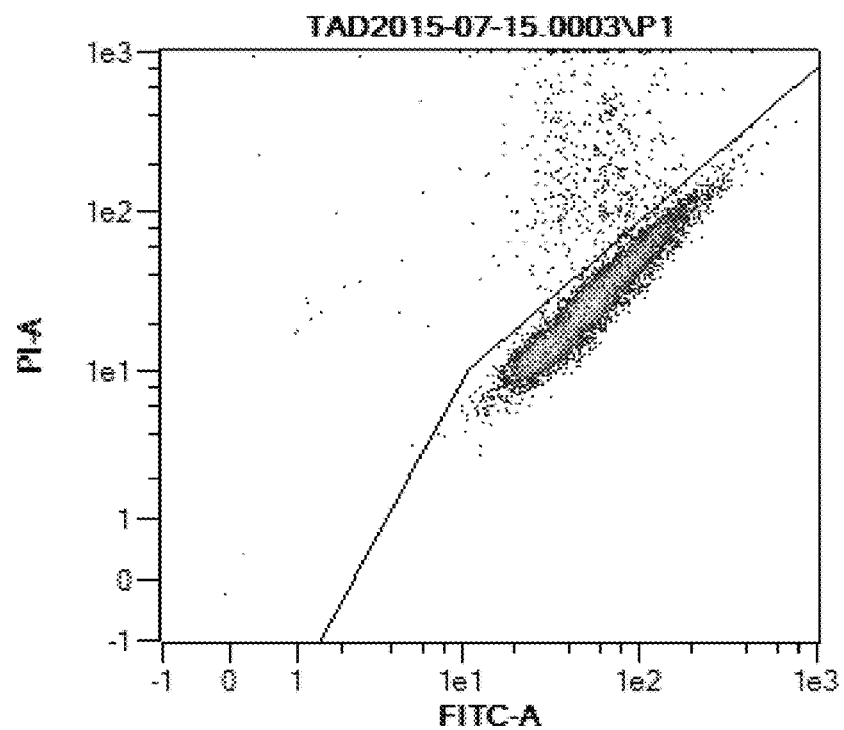

Primary mouse hepatocytes were isolated according to the gold standard (e.g. procedure of Li et al. 2010 in Methods Mol Biol; 633, 185-196). A heating module and a peristaltic pump (flow rate 3.2 ml/min) were calibrated to allow 37° C. at the tubing outlet. After a Balb/C mouse was sacrificed, the animal was secured by taping down the limbs. An incision was made through the skin of the lower abdomen to the lateral aspect of the rib cage and the skin was fold back over the chest. The intestines were moved to the right to reveal the portal vein and the vena cava. A suture were tied loosely around the vena cava near the liver. A cannula was inserted into the vena cava and the suture was secured around the cannula. After removing the inner needle of the cannula, a tubing was connected to the cannula and perfusion medium I (PBS containing 10 mM HEPES, 6.7 mM KCl, 5 mM glucose, and 0.2 mM EDTA, pH7.4) was perfused through the liver Immediately after the start of the perfusion, the portal vein was cut to allow drainage of the blood. After a few seconds the liver clear of blood. After perfusing for 15 min, the tubing was transferred to the bottle of perfusion buffer II (PBS containing 30 mM HEPES, 6.7 mM KCl, 5 mM glucose, 1 mM $CaCl_2$ and collagenase, pH7.4) without introducing air bubbles and the liver was further perfused for 15 min. Then, the perfusion was stopped and the entire liver was carefully excised and transferred to a petri dish containing perfusion medium II. The liver capsule was torn apart with forceps. The sample was carefully triturated with a pipette several times and the cell suspension was transferred to a SmartStrainer, 100 µm. The flow-through was centrifuged for 5 min at 64 g at 4° C. to pellet the hepatocytes. A part of the sample was further purified by a Percoll centrifugation step. For this purpose, the cell suspension was mixed with the same volume of 90% Percoll/10% PBS and centrifuged for 5 min at 64 g. The pellet was washed once in PBS. The resulting single-cells were analyzed on the MACSQuant flow cytometer (FIGS. 6a and 6b). Yield of hepatocytes ($1 \times 10^8/0.8 \times 10^8$ per mouse liver before/after Percoll, respectively) and viability (85/94% before/after Percoll, respectively), measured by taking up propidiumiodid, showed a good performance. Viability was confirmed by microscopic analysis (trypan blue staining). Hepatocytes were successfully taken into culture and survived at least two days.

Comparison Example 2

Combined Mechanical and Enzymatical Liver Dissociation without Perfusion

Figure 7A:
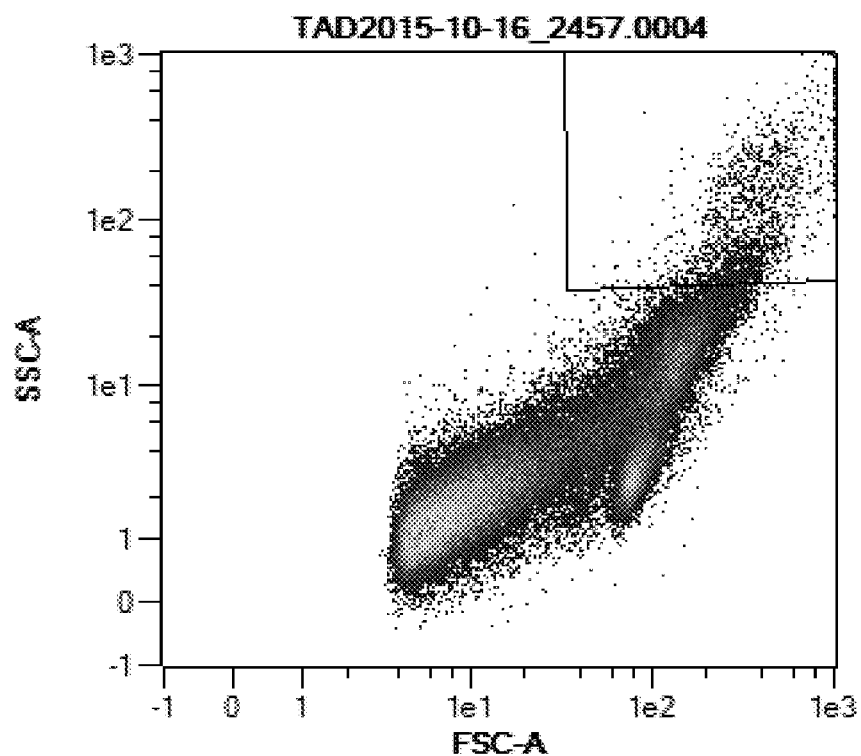
FIGS. 7a and 7b shows the flow cytometry analysis of mouse liver cells isolated by a mechanical/enzymatic protocol without a perfusion step, without further hepatocyte enrichment by Percoll centrifugation.
Figure 7B:
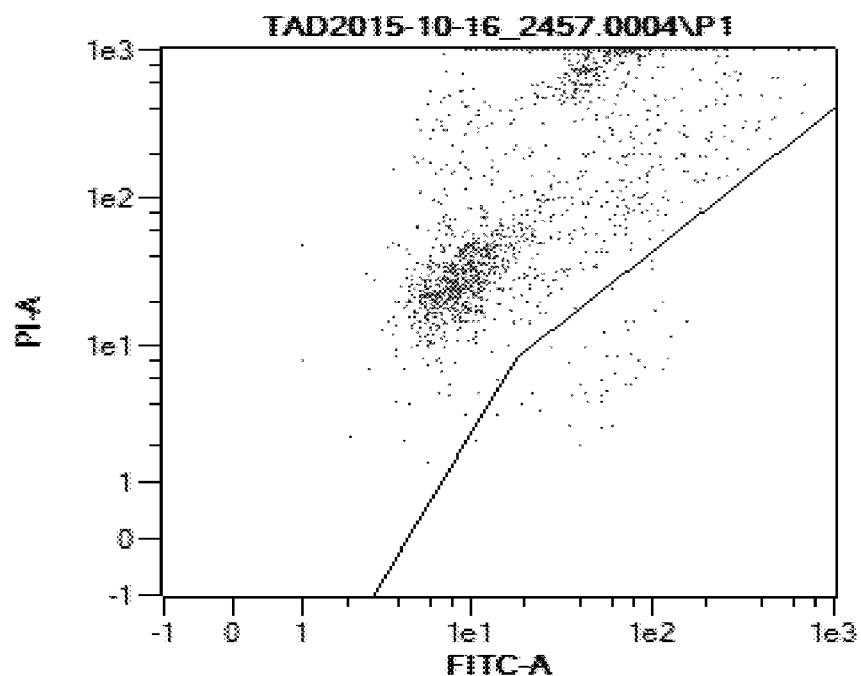

After a CD1 mouse was sacrificed, the liver was carefully excised and transferred to a petri dish containing perfusion medium I. The washed liver was transferred to a gentleMACS C Tube containing 5 ml perfusion medium I and the program h_tumor_03 was started on the gentleMACS Octo to mechanically cut the tissue in smaller fragments. After a 15 min incubation step, the sample was centrifuged and the pellet was once washed in perfusion buffer II. Then, the pellet was incubated for 15 min in perfusion buffer II containing collagenase and DNase. After the incubation, the sample was transferred on a SmartStrainer filter cage available from Miltenyi Biotec GmbH. The flow-through was centrifuged for 5 min at 64 g at 4° C. to pellet the hepatocytes. The resulting single-cells were analyzed on the MACSQuant flow cytometer (FIGS. 7a and 7b). Yield of hepatocytes ($2 \times 10^6$ per mouse liver) and viability (2%), measured by taking up propidiumiodid, was very low. After a Percoll centrifugation step, no cell pellet was visible. Therefore, a combination of mechanical and enzymatical dissociation without perfusion is not useful for getting viable hepatocytes.

Example 3

Perfusion of Mouse Liver with a Hollow Needle Array

A tissue perfusion tool as shown in FIG. 1 with 64 hollow needles (stainless steel; length: 18 mm; inner diameter: 0.19 mm; outer diameter: 0.34 mm) in a plastic holder in a parallel manner was utilized. A peristaltic pump was set to 75 ml/min and a heating module was calibrated to allow 37° C. at the tubing outlet. The outlet of the tubing was connected to the inlet of the pump. In contrast to Comparison Example 1, a tissue perfusion tool containing a hollow needle array was connected to the tubing outlet. After a CD1 mouse was sacrificed, the liver was dissected, washed with PBS on a petri dish and placed onto the nylon mesh of a SmartStrainer. The tissue perfusion tool was filled with perfusion buffer I (see comparative example 1) and simply placed onto the liver so that all hollow needle outlets were inserted into the tissue. After two minutes during which the tissue is freed from blood, a circulation was introduced to reduce the needed buffer volume. For this purpose, a second tubing was used to connect the flow-through and the flask containing the buffer. After 15 minutes, the circulation was stopped by removing the outlet of the second tubing from perfusion buffer I. The inlet of the first tubing was put into a second flask containing perfusion buffer II without introducing an air bubble. After two minutes, a circulation was introduced by connecting the flow-through and the flask containing perfusion buffer II. After 15 minutes, the pump was stopped and the tissue perfusion tool was removed. The perfused tissue was carefully transferred to a petri dish containing 5 ml perfusion buffer II.

Figure 8A:
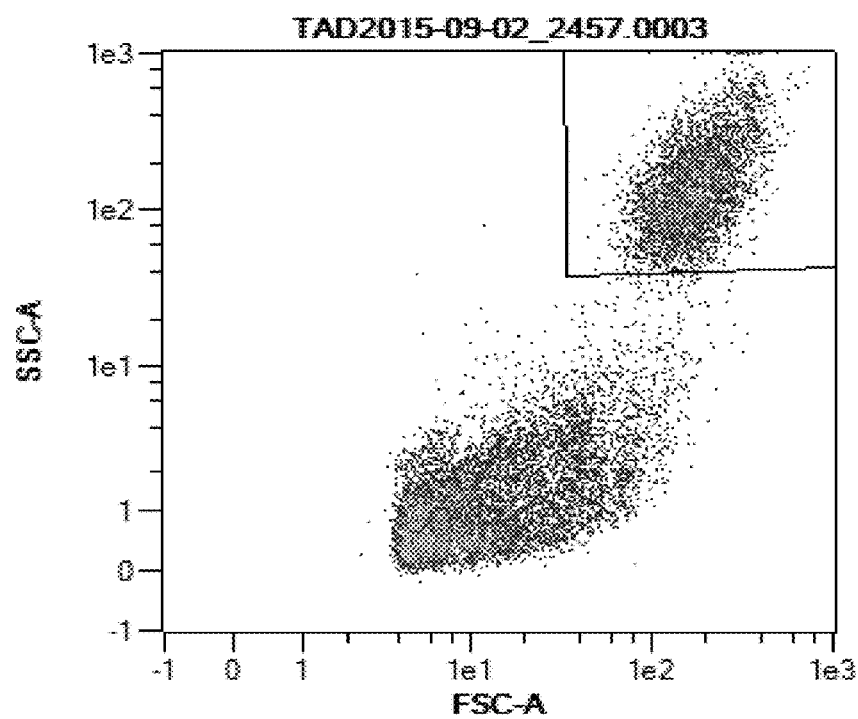
FIGS. 8a and 8b shows the flow cytometry analysis of mouse liver cells prepared according to the invention, with further hepatocyte enrichment by Percoll centrifugation.
Figure 8B:
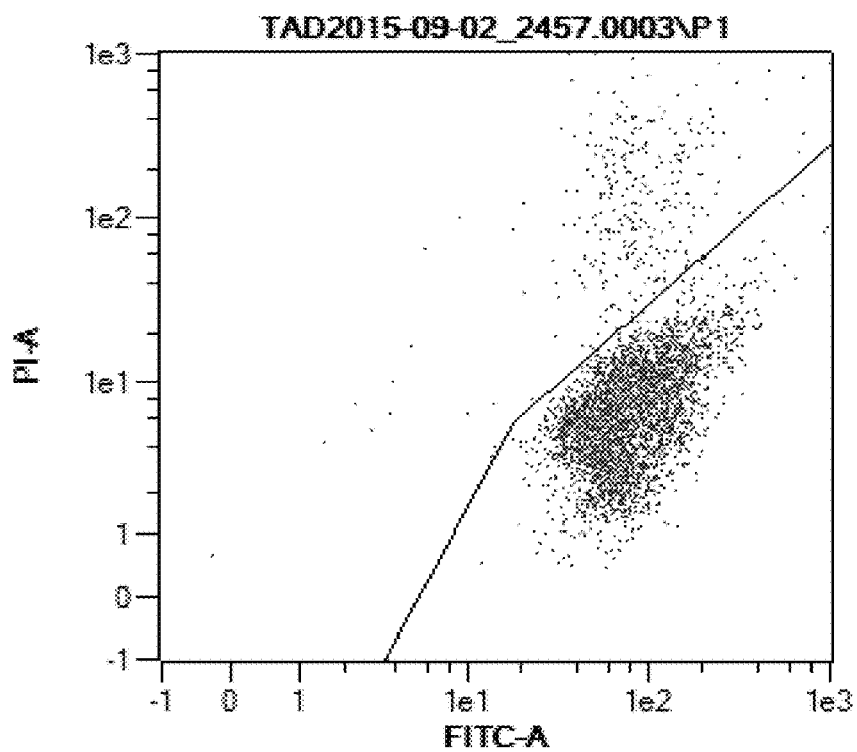

The liver capsule was torn apart with forceps to release the cells. The sample was carefully triturated with a pipette several times and the cell suspension was transferred to a SmartStrainer, 100 µm. The flow-through was centrifuged for 5 min at 64 g at 4° C. to pellet the hepatocytes. A part of the sample was further purified by Percoll gradient centrifugation. The resulting single-cells were analyzed on the MACSQuant flow cytometer (FIGS. 8a and 8b). Yield of hepatocytes ($8.6 \times 10^7/6.6 \times 10^7$ per liver before/after Percoll, respectively) as well as viability (77/92% before/after Percoll, respectively), calculated by propidiumiodid staining, showed excellent results. Hepatocytes were successfully taken into culture and survived at least two days. A comparable performance was achieved with other mouse strains (Balb/C and C57/Bl6).

Example 4

Perfusion of a Rat Liver Lobe with a Hollow Needle Array

Figure 9A:
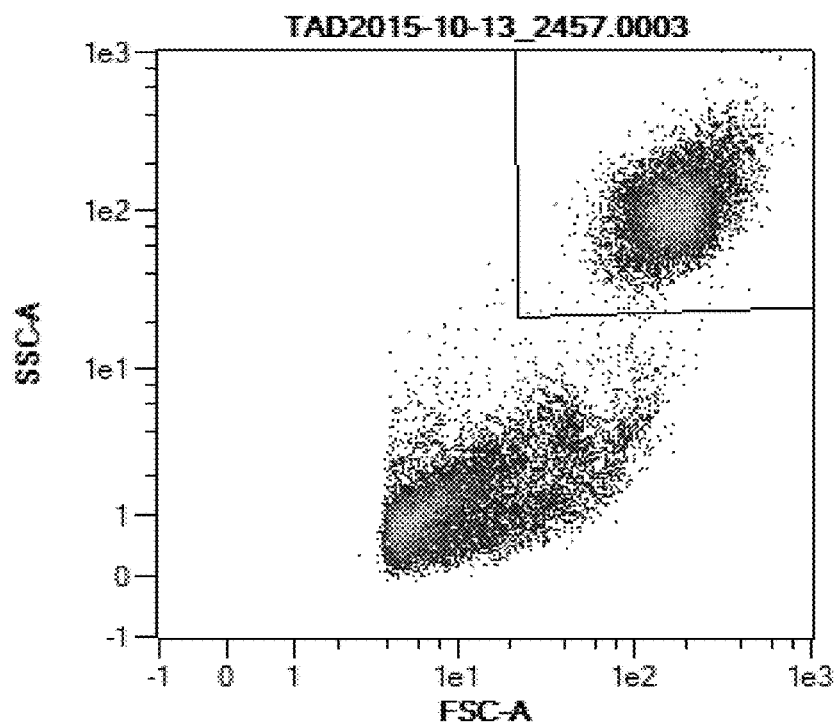
FIGS. 9a and 9b shows the flow cytometry analysis of rat liver cells prepared according to the invention, with further hepatocyte enrichment by Percoll centrifugation.
Figure 9B:
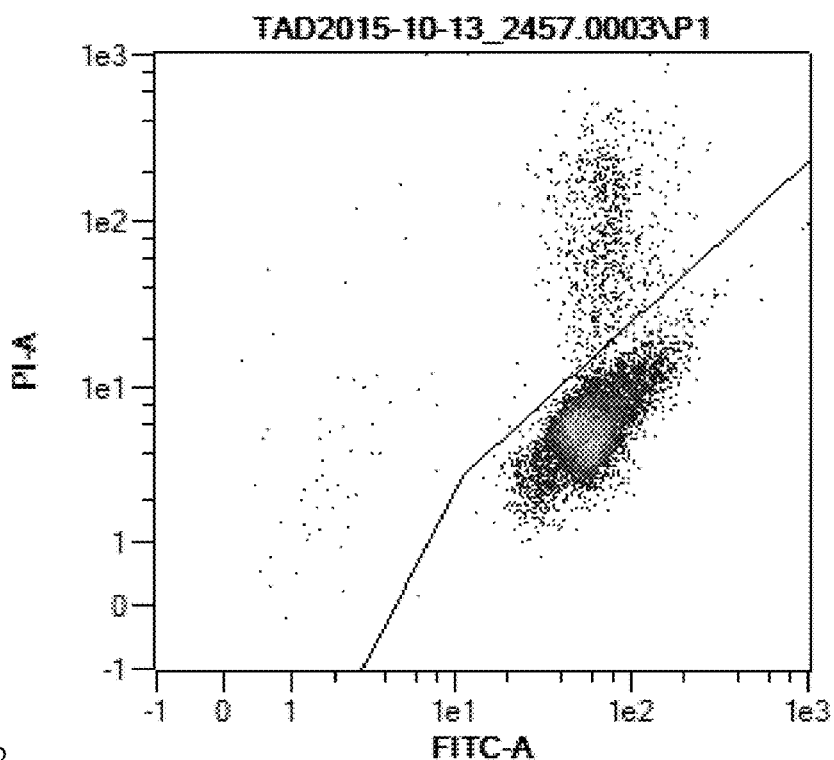

A Wistar rat was sacrificed, and the liver was dissected into single lobes. One of the lobes was processed with the tissue perfusion tool identical to Example 3. The resulting single-cells were analyzed on the MACSQuant flow cytometer (FIGS. 9a and 9b). Yield of hepatocytes ($7.1 \times 10^8/3.7 \times 10^8$ per liver lobe before/after Percoll, respectively) and viability (90/87% before/after Percoll: respectively), calculated by propidiumiodid staining, showed excellent results. A comparable performance was reached with another rat strain (Sprague Dawley).

Example 5

Perfusion of a Mouse Heart with a Hollow Needle Array

A tissue perfusion tool as shown in FIG. 1 but reduced to 7 hollow needles (stainless steel; length: 18 mm; inner diameter: 0.19 mm; outer diameter: 0.34 mm) in a plastic holder in a parallel manner was utilized. A peristaltic pump was set to 30 ml/min and a heating module was calibrated to allow 37° C. at the tubing outlet. The outlet of the tubing was connected to the inlet of the pump. The tissue perfusion tool containing a hollow needle array was connected to the tubing outlet. A CD1 mouse was sacrificed, the chest was opened and the ascending and descending vessels from the heart were blocked by a suture. The vessels were cut next to the suture and the heart was washed with PBS on a petri dish and placed onto the nylon mesh of a SmartStrainer. The tissue perfusion tool was filled with perfusion buffer III (calcium-free Tyrode containing 2,3-Butandione monoxime) and simply placed onto the heart so that all hollow needle outlets were inserted into the tissue. After 90 seconds during which the tissue is freed from blood, a circulation was introduced to reduce the needed buffer volume. For this purpose, a second tubing was used to connect the flow-through and the flask containing the buffer. After 10 minutes, the circulation was stopped by removing the outlet of the second tubing from perfusion buffer III. The inlet of the first tubing was put into a second flask containing perfusion buffer IV (Tyrode containing 2,3-Butandione monoxime with collagenase and trypsin) without introducing an air bubble. After two minutes, a circulation was introduced by connecting the flow-through and the flask containing perfusion buffer IV. After 15 minutes, the pump was stopped and the tissue perfusion tool was removed. The perfused tissue was carefully transferred to a petri dish containing 5 ml Tyrode containing FCS.

Figure 11A:
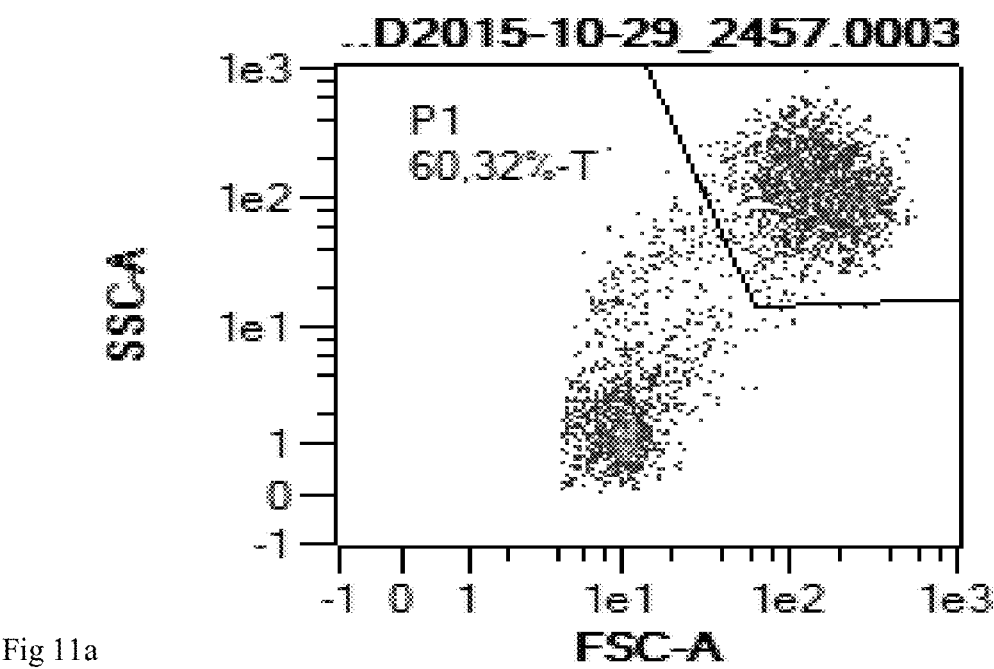
FIGS. 11a and 11b show a sample purified by Percoll gradient centrifugation.
Figure 11B:
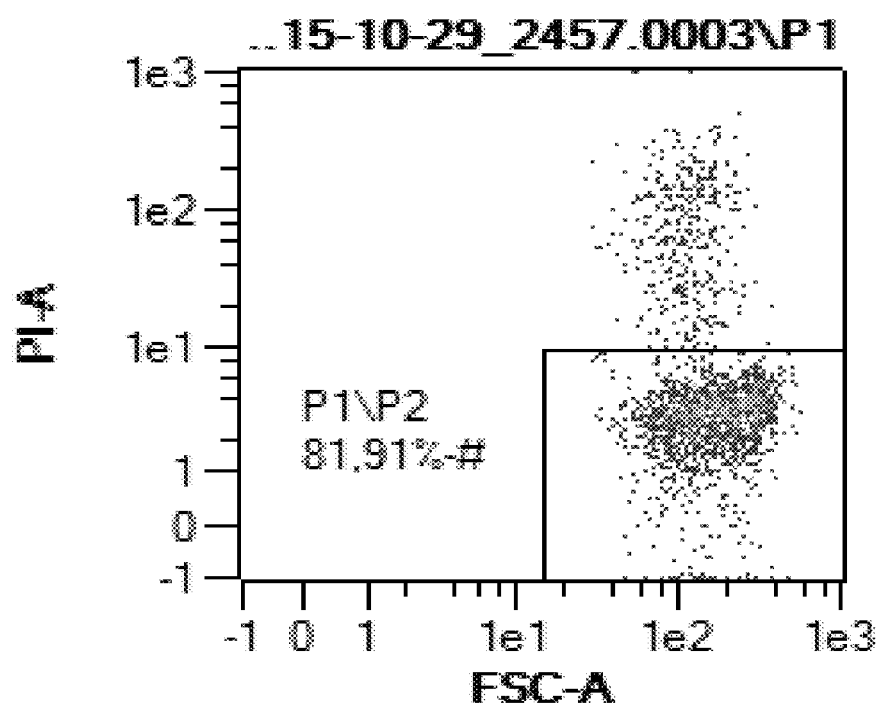
Figure 12:
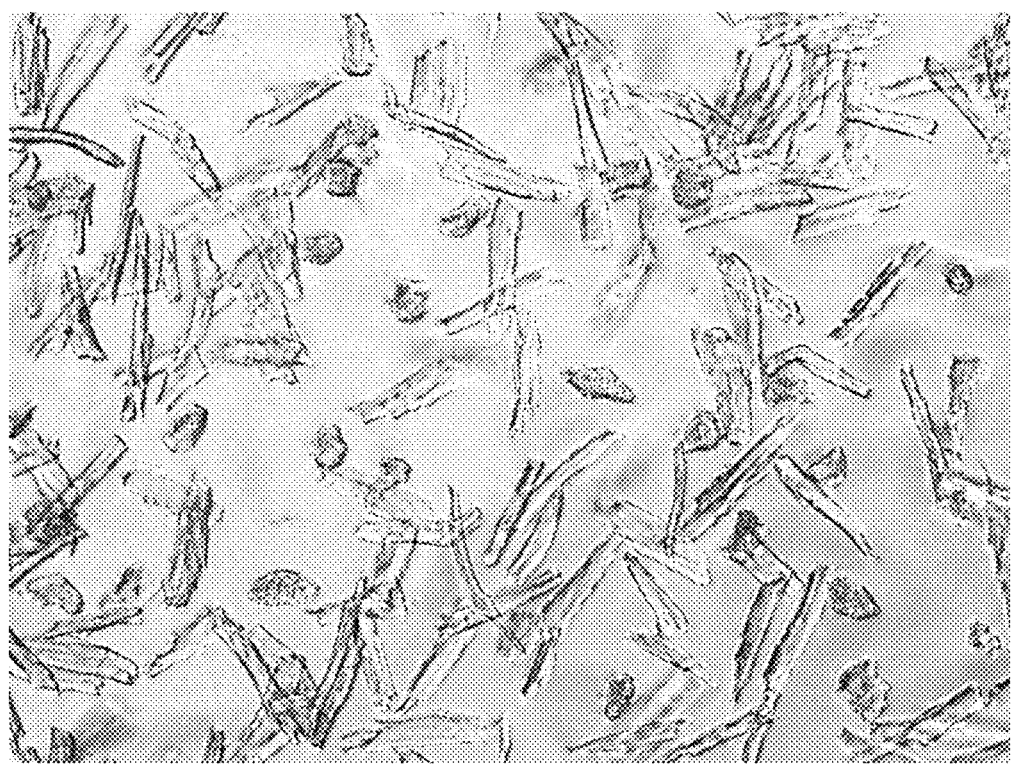
FIG. 12 shows microscopic analysis of primarily typical rod-shaped cardiomyocytes.

The heart capsule was torn apart with forceps to release the cells. The sample was carefully triturated with a pipette several times and the cell suspension was transferred to a SmartStrainer, 100 µm. The flow-through was centrifuged for 1 min at 88 g at 4° C. to pellet the cardiomyocytes. A part of the sample was further purified by Percoll gradient centrifugation. The resulting single-cells were analyzed on the MACSQuant flow cytometer (FIGS. 11a and 11b). Yield of cardiomyocytes ($0.9 \times 10^6$ per heart) having high scatter parameter as well as viability (83%) calculated by propidiumiodid staining, showed good results. Microscopic analysis showed primarily typical rod-shaped cardiomyocytes (FIG. 12).

To sum up, results show that the new procedure using the tissue perfusion tool is an excellent replacement of the state-of-the-art procedure which is complex, inconvenient and can be executed only by staff which is highly trained to find and manipulate the small blood vessels.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A perfusion device for biological tissues, comprising:
   a casing having two parts, a first part (1) and a second part (9);
   a holder (7) for a plurality of hollow penetration structures (8), wherein the hollow penetration structures (8) are provided with at least one orifice having fluid communication through the holder (7);
   and
   a support (5) for the biological tissue (6)
   characterized in that the support (5) for the biological tissue (6) is positioned in the casing at a distance to the holder (7) that by joining the first part (1) and the second part (9) to form the casing, the hollow penetration structures (8) are in proximity to the holder (7)) wherein the first part (1) and the second part have threads disposed thereon, and are opened and closed in a watertight matter using threads disposed on the first part (1) and the second part (2), and wherein the holder for the plurality of hollow penetration structures (8) and the support, are single-use, plastic disposables.

2. The perfusion device according to claim 1, characterized in that by joining the first part (1) and the second part (9) to form the casing, the hollow penetration structures (8) penetrate at least in part into the biological tissue (6).

3. The perfusion device according to claim 1, characterized in that the first part (1) and the second part (9) of the casing are each provided with a corresponding closing mechanism (11, 12) for joining the two parts.

4. The perfusion device according to claim 1, characterized in that the hollow penetration structures (8) extend 1 to 100 mm from the holder (7).

5. The perfusion device according to claim 1, characterized in that the hollow penetration structures (8) are elongated objects having a needle-, cone- or pyramid-like shape.

6. The perfusion device according to claim 1, characterized in that the support (5) is a filter, mesh, rack, grid or a plate with orifices.

7. The perfusion device according to claim 1, characterized in that the holder (7) can be inserted and removed from the casing.

8. The perfusion device according to claim 1, characterized in that the first part (1) and the second part (9) of the casing are provided with a storage cavity (14) for fluids and excess reagent, and further comprising a pump that recirculates the excess reagent and administers it again to the biological sample.

9. The perfusion device according to claim 8, wherein the excess reagent is a disaggregating agent.

10. A process for disaggregation of a biological tissue comprising:
    providing the perfusion device of claim 1;
    penetrating the biological tissue by at least one of the hollow penetration structures (8) by joining the first part (1) and the second part (9) to form the casing with the threads; and
    administering the at least one agent through the hollow penetration structures (8) into the biological tissue (6).

11. The process according to claim 10, wherein the biological tissue (6) is first washed with buffer to remove non-target cells from the biological tissue (6).

12. The process according to claim 10, wherein the agent to disaggregate the biological tissue (6) and/or the buffer is repeatedly administered into the biological tissue (6).

13. The process according to claim 10, wherein the agent to disaggregate the biological tissue (6) is selected from the group consisting of trypsin, chymotrypsin, papain, collagenase, elastase, dispase, thermolysin, hyaluronidase, clostripain and neutral protease from *clostridium histolyticum*, pronase, DNase I, pepsin, proteinase K, lysozyme, chelating agents for bivalent ions and mixtures thereof.

14. The process according to claim 10, wherein the target cells are tissue-resident cells.

15. The process according to claim 10, wherein the biological tissue is selected from the group consisting of spleen, heart, liver, brain and other neural tissues, kidney, lung, pancreas, breast, umbilical cord, skin, placenta, ovary, oviduct, uterus, prostate, tonsil, thymus, stomach, testis, trachea, cartilage, tendon, bone, skeletal muscle, smooth muscle, gut, colon, intestine, bladder, urethra, eye, gall bladder, organoids from cell cultures and tumors.

* * * * *